United States Patent [19]

Bargar et al.

[11] Patent Number: 4,894,389

[45] Date of Patent: Jan. 16, 1990

[54] NOVEL AMINOALKYL-SUBSTITUTED HETEROCYCLIC SULFUR COMPOUNDS

[75] Inventors: Thomas M. Bargar, Clayton, Calif.; Robert J. Borersma, Noblesville; Lawrence C. Creemer, Indianapolis, both of Ind.

[73] Assignee: Merrell Dow Pharmaceuticals Inc., Cincinnati, Ohio

[21] Appl. No.: 104,195

[22] Filed: Oct. 2, 1987

[51] Int. Cl.$^4$ .................. A61K 31/38; C07D 333/12
[52] U.S. Cl. ................................ 514/438; 549/74; 549/75; 549/76
[58] Field of Search .................. 549/32, 35, 39, 49, 549/58, 74, 75, 76, 438

[56] References Cited

U.S. PATENT DOCUMENTS 3,839,321 10/1974 Weinstock ........................ 549/77

OTHER PUBLICATIONS

Chamberlin, R. A. and Chung, J. Y. L., *J. Org. Chem.* 50, 4425–4431, 1985.
Fitzpatric, P. F. and Villafranca, J. J., *J. Biol. Chem.*, 261(10), 4510–4518, 1986.
Miller, S. M. and Klinman, J. P., *Biochemistry*, 24, 2214–2127, 1985.
Hamberger, H., Stutz, P., and Schultz, G., *Tetrahedron Letters*, 41, 3623–3624, 1977.
Gordon, A. A., Feigen, G. A., Journal of Pharmacology and Experiments in Therapeutics, 72, 265–275, (1941).

*Primary Examiner*—Alan Siegel
*Attorney, Agent, or Firm*—Alice A. Brewer

[57] ABSTRACT

The invention relates to novel aminoalkyl substituted heterocyclic sulfur compounds which are useful as antihypertensive agents.

6 Claims, No Drawings

NOVEL AMINOALKYL-SUBSTITUTED HETEROCYCLIC SULFUR COMPOUNDS

This invention relates to novel aminoalkyl-substituted cyclic heterocyclic sulfur compounds, to processes and intermediates useful for their preparation, and to pharmaceutical compositions containing said compounds as well as methods of treating hypertension with said compounds.

More specifically, this invention relates to aminoalkyl-substituted heterocyclic sulfur compounds of the general formula

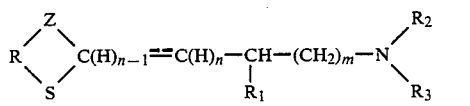

wherein
the dotted line indicates the optional presence of a double bond,
m is an integer from 0 to 4,
n is the integer 1 or 2 depending on whether a double bond is present,
Z is a methylene or sulfur,
R is ethylene, vinylene or ortho-phenylene with the proviso that when Z is methylene, R must be ethylene,
$R_1$ is hydrogen or lower alkyl,
$R_2$ is hydrogen, lower alkyl, hydroxy, amino, or amidino, and
$R_3$ is hydrogen or lower alkyl,
and the therapeutically acceptable acid addition salts thereof. These compounds possess dopamine β-hydroxylase inhibitory properties or other properties which make them useful in the treatment of hypertension.

The term "methylene" in each occurrence refers to the formula —CH$_2$—. The term "lower alkyl" in each occurrence means straight- or branched-chain alkyl groups of from one to six carbon atoms and include methyl, ethyl, propyl, butyl, pentyl and hexyl groups. When $R_2$ is amino and $R_3$ is hydrogen, the —NR$_2$R$_3$ moiety is a hydrazino radical and when $R_2$ is amidino and $R_3$ is hydrogen, the —NR$_2$R$_3$ moiety is a guanidino radical.

When $R_1$ is lower alkyl, m is preferably zero, and straight-chained lower alkyl groups of from one to three carbon atoms are employed at the $R_1$ position. In another preferred embodiment, $R_1$ is preferably hydrogen and $R_2$ is a straight-chained lower alkyl group of from one to three carbon atoms. In an additional preferred embodiment, $R_2$ and $R_3$ are preferably hydrogen.

One preferred group of compounds are those wherein Z is methylene. Another preferred group of compounds are those wherein Z is sulfur. When Z is sulfur, R is preferably ethylene or vinylene. All possible sterioisomers and geometric isomers of appropriate compounds are within the scope of this invention.

Illustrative examples of the compounds of this invention include:
2-[1,3-(benzodithiolan-2-ylidene)]ethanamine,
2-(1,3-dithiolan-2-ylidene)ethanamine,
[2-(1,3-dithiolan-2-ylidene)ethyl]hydrazine,
2-(1,3-dithiol-2-ylidene)ethanamine,
[2-(1,3-dithiolan-2-ylidene)ethyl]guanidine
1,3-dithiolane-2-ethanamine,
1,3-dithiolane-2-propanamine,
1-(1,3-dithiolan-2-ylidene)-2-propanamine,
1-(1,3-dithiolan-2-ylidene)-2-butanamine,
(E)-2-(dihydro-2(3H)-thienylidene)ethanamine
2-(4-methyl-1,3-dithiolan-2-ylidene)ethanamine, Representative salts are those salts formed with non-toxic organic or inorganic acids, such as, for example, those formed from the following acids: hydrochloric, hydrobromic, sulfonic, sulfuric, phosphoric, nitric, maleic, fumaric, benzoic, ascorbic, succinic, methanesulfonic, acetic, propionic, tartaric, citric, lactic, malic, mandelic, cinnamic, palmitic, itaconic, benzenesulfonic, and toluenesulfonic.

The particular process path to be utilized in the preparation of the compounds of this invention depends upon the specific compound desired. Such factors as the saturation or unsaturation of the heterocyclic moiety, the presence of one sulfur atom or two sulfur atoms in the heterocyclic moiety, and the specific substituents of $R_1$ and $R_2$ all play a role in the path to be followed in the preparation of the specific compounds of this invention. Those factors are readily appreciated by one of ordinary skill in the art. However, in general, the compounds of this invention may be prepared by standard techniques and processes analogously known in the art.

In those instances where the formula I compounds desired are amines containing Z as sulfur, $R_1$ as hydrogen, $R_2$ as amidino or hydrogen and m as zero, and when R is not vinylene, (group $I_a$ below) appropriate nitriles such as 1,3-dithian- or 1,3-dithiol-2-ylideneacetonitrile ($IV_a$), are reduced with excess diisobutylaluminum hydride (DIBAL-H) in an organic solvent such as toluene at a temperature of about 70° C. to about 110° C., preferably at 90° C., under an inert atmosphere to produce the compounds in group $I_a$. The nitriles ($IV_a$) are produced by reacting carbon disulfide (CS$_2$) with acetonitrile ($II_a$) in the presence of lithium diisopropylamide (LDA) in ether at about −70° C. to make the dithioanion ($III_a$). $III_a$ can then alkylate the appropriate alpha, omega dibrominated agent, or orthodibromobenzene (RBr$_2$) in an organic solvent such as dimethylformamide (DMF) or hexamethylphosphoramide (HMPA) at elevated temperatures to produce $IV_a$. This synthetic route is depicted in Reaction Scheme A:

REACTION SCHEME A

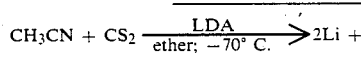

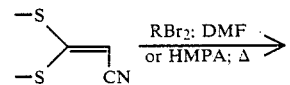

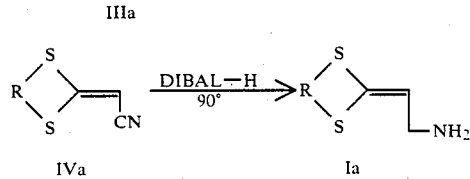

The compound containing R as vinylene and Z as sulfur ($I_b$) can be produced by allowing dithiolylideneethylphthalimide ($VI_b$) to react with hydrazine in a highly polar organic solvent such as methanol (MeOH) at a temperature of about 25° C. to about 65° C. VI$_b$ is produced by partially hydrolyzing the diester, 1,3-dithio-2-ylidenepropanedioic acid diethyl ester (II$_b$) to the diacid monoester (III$_b$) with potassium hydroxide (KOH) in ethanol (EtOH) under reflux conditions, and then decarboxylating (III$_b$) to its monoacid ester (IV$_b$) with p-toluenesulfonic acid (pTSA) in ethanol at a temperature of about 40° C. to about 80° C., preferably at about 60° C. The ester is reduced with DIBAL-H at a temperature of about −100° C. to about −40° C., preferably at −70° C., 3 and then converted to VI$_b$ by reacting the alcohol (V$_b$) with triphenylphosphine (⌀$_3$P), diethyl azodicarboxylate (DEAD), and phthalimide in tetrahydrofuran (THF) at about 25° C. This synthetic route is depicted in Reaction Scheme B:

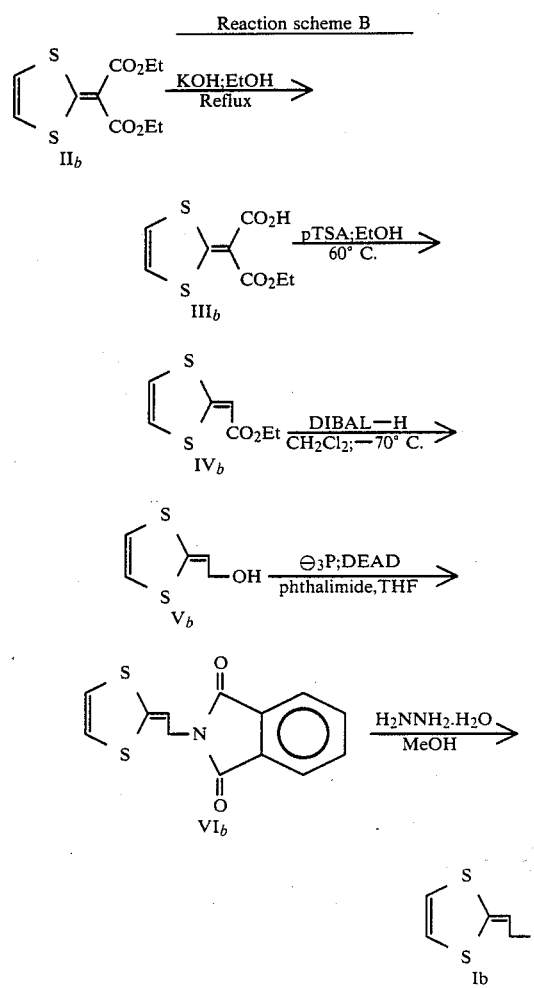

The compounds wherein Z is sulfur, R is other than vinylene, R$_1$ is lower alkyl (I$_c$) are obtained by the reduction of an appropriate azide such as 1-(1,3-dithiolan-2-ylidene)-2-propylazide (VI$_c$) with lithium aluminum hydride (LiAlH$_4$) in ether at a temperature of about −40° C. to about 0° C., preferably at −5° C. to −10° C. The appropriate azides are produced by reacting a methylketone such as acetone (II$_c$) with carbon disulfide (CS$_2$) in benzene containing sodium t-amyl alcoholate (Na-amyl alcoholate) to produce III$_c$ which is then reacted with the appropriate alpha, omega dibrominated agent (RBr$_2$) in acetonitrile (CH$_3$CN) resulting in the ketone IV$_c$, which is then reduced with sodium borohydride (NaBH$_4$) in methanol at a temperature of about 25° C. to about 60° C., preferably at 40° C. to 50° C., to its alcohol (V$_c$) which is then converted to the desired VI$_c$ with ⌀$_3$P, carbon tetrabromide (CBr$_4$) and lithium azide (LiN$_3$) in dimethylformamide (DMF) at a temperature between about −10° C. to 60° C. This synthetic route is depicted in Reaction Scheme C:

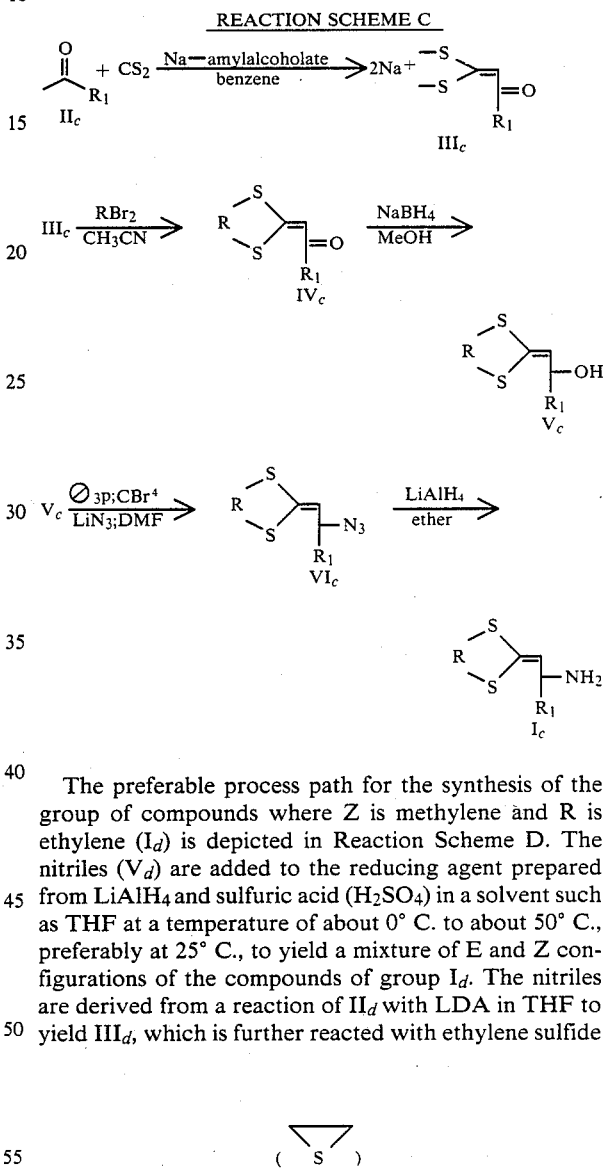

The preferable process path for the synthesis of the group of compounds where Z is methylene and R is ethylene (I$_d$) is depicted in Reaction Scheme D. The nitriles (V$_d$) are added to the reducing agent prepared from LiAlH$_4$ and sulfuric acid (H$_2$SO$_4$) in a solvent such as THF at a temperature of about 0° C. to about 50° C., preferably at 25° C., to yield a mixture of E and Z configurations of the compounds of group I$_d$. The nitriles are derived from a reaction of II$_d$ with LDA in THF to yield III$_d$, which is further reacted with ethylene sulfide

in THF resulting in IV$_d$. IV$_d$ was cyclized and dehydrated with camphorsulfonic acid (CSA) in benzene under reflux conditions to yield V$_d$.

Reaction scheme D

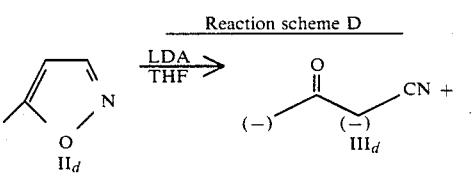

-continued
Reaction scheme D

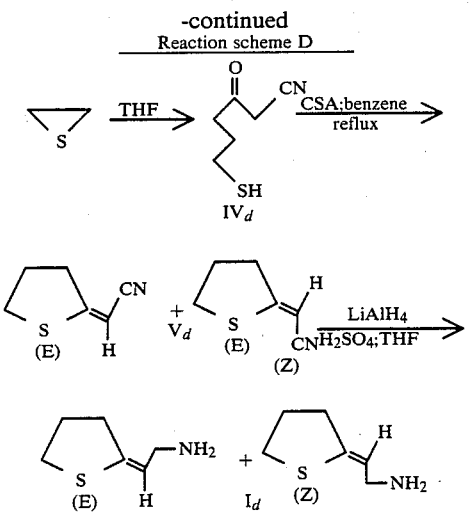

An alternative procedure is described in Example 6 which makes use of carboxylic acid esters corresponding to the nitriles above. These are reduced to the corresponding alcohols which are then converted to the desired amines by the procedure described in Example 6.

Additionally, guanidino compounds (where $R_2$ is amidino and $R_3$ is hydrogen) can be produced by reacting any group I compound (i.e., $I_a$, $I_b$, etc.) with cyanamide at elevated temperatures. Compounds wherein n is two can be produced by the acid catalyzed reduction of any group I compound by trifluoroacetic acid and triethylsilane at a temperature of about $-20°$ C. to about $40°$ C., preferably at $20°$ C. Hydroxylamine compounds (where $R_2$ is hydroxy and $R_3$ is hydrogen) can be made by reducing the appropriate nitrile $IV_a$ with DIBAL-H at a temperature of about $-40°$ C. to about $-100°$ C., preferably at $-70°$ C., then adding $H_2O$ to form an aldehyde which, in the presence of hydroxylamine, is converted to the corresponding oxime. The oxime can be reduced by sodium cyanoborohydride at a pH of about 4 to 6 to form the appropriate hydroxylamine. Hydrazino compounds (where $R_2$ is amine and $R_3$ is hydrogen) can be derived from an appropriate aldehyde described above by reducing it with DIBAL-H at a temperature of about $-40°$ C. to about $-100°$ C., preferably at $-70°$ C., to form an alcohol which can react with carbon tetrabromide in the presence of triphenylphosphine at a temperature of about $0°$ C. to about $40°$ C., preferably at $25°$ C., to form the appropriate brominated compound which, when combined with hydrazine in methanol, is converted to the appropriate hydrazino compound. The various compounds encompassed within this invention can be obtained from starting materials described generally herein using conventional and well known methodology.

The acid addition salts of the compounds of this invention can also be readily prepared by conventional chemical methodology.

The foregoing reaction schemes are further illustrated by the following specific examples:

EXAMPLE 1

2-(1,3-Dithiolan-2-ylidene)ethanamine

N,N-Diisopropylamine (28.0 ml, 0.2 mol) was dissolved in 125 ml ether under nitrogen in a three-necked flask equipped with mechanical stirrer, thermometer, and nitrogen bubbler. The solution was cooled to $-10°$ C. and n-butyllithium (3.1M in hexane, 64.5 ml, 0.2 mol) was added dropwise with stirring. After 10 minutes, the solution was cooled to $-70°$ C. and $CH_3CN$ (5.2 ml, 0.1M) in 15 ml ether was added dropwise keeping the temperature below $-65°$ C. When addition was complete, $CS_2$ (6.0 ml, 0.1 mol) in 15 ml ether was added dropwise, again keeping the temperature below $-65°$ C. When the addition was complete, the solution was warmed to $0°$ C. and allowed to stir for one hour. The crude salt was filtered and washed several times with ether and the solvent removed under vacuum; 13.43 g of the salt $III_a$ was produced.

A solution of 0.769M $III_a$ salt in 780 ml (0.6 mol) DMF was cooled to $0°$ C. and 1,2-dibromoethane (70 ml, 0.81 mol) in 100 ml DMF was added dropwise. When addition was complete, the solution was stirred at $25°$ C. for 1 hour, then diluted with water and extracted with ether. The ether was washed with water, then brine, dried over $K_2CO_3$ and evaporated. The nitrile product was distilled (bulb-to-bulb) at $110°$ C./0.05 torr yielding a yellow oil in 40% yield. This nitrile (10.95 g, 0.077 mol), in 25 ml toluene, was added dropwise to a solution of DIBAL-H (1.5M in toluene, 153.8 ml, 0.23 mol) which had been heated to $90°$ C. under nitrogen. This mixture was stirred 5 minutes at $90°$ C., then was cooled to $0°$ C. and quenched by dropwise addition of 5N sodium hydroxide. The resulting gel was diluted with water and extracted with ether. The ether extract was washed with brine, dried over $K_2CO_3$ and evaporated, yielding a yellow oil. The oil was distilled (bulb-to-bulb) at $100°$ C./0.1 torr yielding 3.95 g (35%) product. The tosylate salt was precipitated from the ether by adding 1M pTSA in ethanol and recrystallizing from ethyl acetate/ethanol, yielding 4.7 g (19%) of the title compound as a tosylate salt.

MP $155°-156°$ C. (dec.); Anal Calcd for $C_{12}H_{17}NO_3S_3$: C, 45.12; H, 5.36; N, 4.38; Found: C, 45.31; H, 5.43; N, 4.50.

EXAMPLE 2

1,3-Dithiolane-2-ethanamine

The product described in Example 1 (200 mg, 0.626 mmol), trifluoroacetic acid (0.36 ml, 4.72 mmol), and triethylsilane (0.18 ml, 1.14 mmol) were combined in 2 ml methylene chloride and stirred at $25°$ C. for 10 minutes. The solution was diluted with 1N sodium hydroxide and extracted with ether. The ether extract was washed with brine, dried ($K_2CO_3$) and evaporated leaving the crude title amine. The tosylate salt of the title compound was precipitated from ether by the addition of 0.6 ml 1M pTSA in ethanol yielding 110 mg (55%).

MP $119°-121°$ C. (sublimes); Anal. CalCd for $C_{12}H_{19}NO_3S_2$: C, 44.83; H, 5.96; N, 4.36; Found: C, 44.82; H, 6.11; N, 4.39.

EXAMPLE 3

2-(1,3-Dithiol-2-ylidene)ethanamine 1,3-Dithio-2-ylidenepropanedioic acid diethyl ester ($II_b$), Was produced according to procedures set forth in U.S. Pat. No. 4,327,223. The diester (7.8 g, 30 mmol) was combined with potassium hydroxide (3.37 g, 60 mM) in 100 ml ethanol and heated to reflux for 4 hours. The reaction mixture was cooled and poured into 1N hydrochloric acid. The resulting precipitate was filtered and dried yielding 4.67 g of the diacid monoester (67%).

The monoester (16.79 g, 72.4 mmol) was suspended in 250 ml absolute ethanol containing pTSA (0.5 g, 2.63 mmol) and heated to 60° C. for 1.5 hours. The reaction mixture was cooled, and undissolved solids were removed by filtration. The filtrate was diluted with water and extracted with ether, the latter washed with brine, dried ($K_2CO_3$) and evaporated. The product was distilled (bulb-to-bulb) at 150° C./1.0 torr yielding 10.24 g of pure monoacid ester (75%). The monoacid ester (1.41 g, 7.5 mmol) was dissolved in 10 ml $CH_2Cl_2$, cooled to −70° C. under nitrogen, and DIBAL-H (1.5M in toluene, 15.5 ml, 23.3 mmol) was added dropwise to maintain the reaction temperature below −60° C. The reaction was then quenched by the addition of 7.2 ml 5N sodium hydroxide at −70° C., diluted with water, and extracted with ether. The ether extract was washed with brine, dried ($K_2CO_3$) and evaporated at 25° C. to a solution of the crude unstable alcohol in toluene.

Triphenylphosphine (4.2 g, 15 mmol) and phthalimide (4.72 g, 32 mmol) were dissolved in 10 ml THF and diethyl azodicarboxylate (2.95 g, 16 mmol) in 5 ml THF was added dropwise. This solution was allowed to stir 30 minutes and then the crude alcohol obtained as described in the preceding paragraph, in 1 ml THF was added dropwise at 25° C. This reaction mixture was allowed to stir 10 minutes, then diluted with 300 ml 1N sodium hydroxide and extracted with ether. The ether solution was dried over $K_2CO_3$ and evaporated and the product was separated by flash chromatography (silica gel, 20% diethyl ether:20% ethyl acetate in hexane) and recrystallized from hexane/ethyl acetate to provide 510 mg of the phthalimide. This product (340 mg, 1.23 mmol) was suspended in 26 ml methanol, and hydrazine monohydrate (0.67 ml, 13.8 mmol) was added and the mixture was allowed to stir at 25° C. for 20 minutes. The mixture was concentrated under high vacuum, then diluted with 1N sodium hydroxide and extracted with ether. The ether was washed with brine, dried ($K_2CO_3$) and evaporated at 25° C. yielding 130 mg yellow oil. The oil was dissolved in ether, and 0.5 ml 1N pTSA in ethanol was added to produce 130 mg (33%) of the title compound as its tosylate salt.

Mp 95°–125° C. (dec.); Anal. Calcd for $C_{12}H_{15}NO_3S_3$: C, 45.40; H, 4.76; N, 4.41; Found: C, 45.82; H, 4.88; N, 4.71.

EXAMPLE 4

1-(1,3-Dithiolan-2-ylidene)-2-propanamine

The ketone $IV_c$ (Reaction Scheme C) wherein R is ethylene and $R_1$ is methylene, was produced by the method of Thullier, A. and Vialle, *J. in Bull. Soc. Chem. Fr.*, 1962, 2182. The ketone (3.0 g, 18.75 mmol) was dissolved in 45 ml absolute methanol and $NaBH_4$ (3.6 g, 93.75 mmol) was added as a solid, in small portions, keeping the temperature below 50° C. The reaction mixture was allowed to stir for 30 minutes at 25° C. It was then diluted with water and extracted with dichloromethane ($CH_2Cl_2$). The extract was dried ($K_2CO_3$) and evaporated yielding 3.0 g (99%) of crude alcohol. The alcohol(10.37 g, 63.97 mmol) and triphenylphosphine (50.35 g, 191.4 mmol) were dissolved in 250 ml DMF and cooled to 0° C. Carbon tetrabromide (50.76 g, 210.4 mmol) was added in two portions allowing the solution to warm to 45° C.

After lowering the temperature of the reaction mixture to 10° C., lithium azide (15.18 g, 312 mmol) was added, and the reaction was allowed to stir for 4 hours in the dark. It was then diluted with water and extracted with ether. The ether extract was washed with water, then brine, and dried over $K_2CO_3$. The solvent was evaporated at 25° C. and the resulting crude azide was purified by flash chromatography (silica gel, 5% ether in pentane). Further evaporation on a lukewarm water bath under aspirator vacuum yielded 7.12 g (60%) azide. The azide (7.13 g, 38.07 mmol) in 50 ml ether was added dropwise in the dark to lithium aluminum hydride (2.1 g, 55.4 mmol) which had been suspended in ether under nitrogen and cooled to −7° C. The reaction mixture was allowed to stir at −7° C. for 30 minutes. It was then warmed to 0° C. and quenched by the addition of 2.1 ml water, followed by 2.1 ml 15% sodium hydroxide and finally 6.3 ml water. The resulting solid was filtered through diatomaceous earth and washed with ether. The filtrate was collected and the solvent evaporated. The crude product was distilled (bulb-to-bulb) at 125° C./0.5 torr to yield 2.27 g (37%) pure product. The tosylate salt of the title compound was formed by dissolving the pure amine in ether under nitrogen and slowly adding 0.95 equivalent 1M pTSA in ethanol. MP 165°–170° C. (dec); Anal Calcd for $C_{13}H_{19}NO_3S_3$: C, 46.82; H, 5.74; N, 4.20; Found: C, 47.02; H, 5.91; N, 4.18.

EXAMPLE 5

(E)-2-(Dihydro-2(3H)-thienylidene)ethanamine

The dilithio anion of cyanoacetone was prepared (following the procedure set forth in Vinick, F. J.; Pay, Y.; Gschwend, H. W., *Tetrahedron Letters*, 1978, 44, 4221) from 49.3 ml (0.6 mol) 5-methylisoxazole in 800 ml THF. The anion was cooled to −16° C. and ethylene sulfide (32.2 ml, 9.54 mol) was added dropwise over 45 minutes. The reaction mixture was then allowed to warm to 25° C. and stirred for 18 hours. It was quenched by the addition of 1 liter water with cooling, and neutralized with glacial acetic acid. The organic layer was separated and the aqueous layer was extracted with ethyl acetate. The organic layers were combined, washed with brine, dried over $MgSO_4$ and evaporated. The resulting oil was distilled (bulb-to-bulb) at 160° C./0.4 torr to yield 22.8 g intermediate product ($IV_d$), which was dissolved in 500 ml dichloromethane containing camphorsulfonic acid (22 g, 0.095 mol) and stirred for 15 minutes at 25° C. The reaction mixture was washed with 1N sodium hydroxide and the aqueous layer was saturated with sodium chloride and extracted with ethyl acetate. The organic layers were combined, dried ($MgSO_4$) and evaporated. The products were purified by liquid chromatography (10% ethyl acetate in hexane) to give the individual pure nitrile Z and E isomers.

Lithium aluminum hydride (0.31 g, 8.06 mmol) was suspended in 10 ml THF under nitrogen and concentrated sulfuric acid (0.22 μl, 4.06 mmol) was added slowly and the solution was stirred 1 hour. The nitrile E isomer (0.5 g, 4.06 mmol) in 6 ml THF was added slowly, and this reaction mixture was allowed to stir for three hours at 25° C. The reaction mixture was quenched by the sequential addition of 280 microliters water, 509 microliters 15% sodium hydroxide and 765 microliters water. The resulting solid was filtered through diatomaceous earth and washed with THF. The filtrates were combined and evaporated and the product was purified by flash chromatography (silica gel, 2% ammonium hydroxide: 18% methanol in chloroform) to yield 200 mg (38%) pure product. The tosylate salt of the title compound was formed by dissolving the product in water and precipitating out the salt by the addition of 1 M p-TSA in ethanol and recrystallizing it from ethyl acetate/ethanol.

MP 135°-137° C., Anal. Calcd for $C_{13}H_{19}NO_3S_2$: C, 51.80; H, 6.35; N, 4.65; Found C, 51.64; H, 6.46; N, 4.67.

EXAMPLE 6

(Z)-2-Dihydro-2(3H)-thienylidene)ethanamine

The monosodium, monolithium dianion of ethyl acetoacetate was formed by the method of Weiler, I., *J. Amer. Chem. Soc.*, 92, 6702 (1970). A suspension of 0.1 mol dianion in 200 ml THF was cooled to 5° C. under $N_2$ and ethylene sulfide (5.65 ml, 0.095 mol) was added dropwise slowly. The reaction mixture was then diluted with 100 ml water and brought to a slightly basic pH with 5N HCl. The organic layer was separated and the aqueous layer was extracted with ether. The organic layers were combined, washed with saturated $NaHCO_3$, brine, and dried ($Na_2SO_4$). The solvent was evaporated giving 16.55 g of a yellow oil. The oil was dissolved in 800 ml of $CH_2Cl_2$ and refluxed with 16.55 g oxalic acid for 3 hours. It was then cooled and the solids were filtered. The filtrate was washed with 1N NaOH, dried ($K_2CO_3$), and the solvent was evaporated. The resulting product mixture was distilled (bulb-to-bulb) at 150° C./0.6 torr giving a light yellow oil (4.81 g, 30%).

The mixture of Z/E esters (3.95 g, 22.97 mmol) obtained as a product of the preceding paragraph was mixed with 20 ml of $CH_2Cl_2$ and this mixture was added dropwise to DIBAL-H (1.5M in toluene, 45.92 ml, 68.76 mmol) at −70° C. under $N_2$. The reaction temperature was maintained below −55° C. When the addition was complete, the reaction mixture was stirred at −70° C. for 15 minutes, quenched with 5N NaOH (at −70° C. ) and allowed to warm to 25° C. The solution was diluted with water and extracted with $CH_2Cl_2$. The $CH_2Cl_2$ was dried ($Na_2SO_4$) and evaporated with slight heating. The Z/E alcohols were separated by flash chromatography (silica, 40% EtOAc in hexane) giving a 20:1 Z/E ratio with a yield of 72%. The Z alcohol (0.2 g, 1.5 mmol) was dissolved in 24 ml THF containing triphenylphosphine (0.8 g, 3.07 mmol), and 0.95M hydrazoic acid in benzene (6.45 ml, 6.13 mmol). Diisopropyl azodicarboxylate (0.62 g, 3.07 mmol) in 2.4 ml THF was added dropwise at 0° C. (in the dark). When the addition was completed, the reaction mixture was stirred at 0° C. for 45 minutes, then diluted with water and extracted with ethyl acetate. The ethyl acetate extract was washed with brine, dried ($MgSO_4$) and evaporated. The product was purified by flash chromatography (silica gel, 3% ether in pentane) giving the Z/E azides as an inseparable mixture (0.17 g, 73%).

A mixture of the Z/E azides (1.15 g, 7.42 mmol) was dissolved in 16 ml ether and added dropwise to a suspension of lithium aluminum hydride (0.41 g, 10.72 mmol) in ether under $N_2$ at −5° C. (in the dark). When the addition was complete, the reaction mixture was stirred at −10° C. for 30 minutes and was then quenched by addition of 0.41 ml of water, followed by 0.41 ml of 15% NaOH, and then 1.23 ml water. The resulting solid was filtered through diatomaceous earth and washed with ether. The filtrate was evaporated at 25° C. to give an opaque oil. The Z amine was separated by flash chromatography (silica, 20% MeOH/5% $NH_4OH$ in ether), and the tosylate salt thereof was precipitated from ether by addition of 1M pTSA in ethanol, giving the title amine salt as a white solid (1.08 g, 48%). MP 134°-136° C; Anal Calcd for $C_{13}H_{19}NO_3S_2$: C, 51.80; H, 6.35; N, 4.65; Found: C, 51.79; H, 6.36; N, 4.61.

The compounds of this invention are dopamine-β-hydroxylase (DBH) inhibitors or lower blood pressure by other mechanisms, therefore they are expected to be valuable therapeutic agents useful in the treatment of hypertension. An embodiment of this invention thus comprises a method of treating hypertension in a mammal which comprises administering internally to said mammal a composition containing an effective antihypertensive amount of compound of formula I.

The utility of the present compounds as antihypertensive agents can be demonstrated by the following procedures.

Since DBH is a major enzyme in the synthetic pathway of norepinephrine (NE), the presence of a DBH inhibitor would act to decrease the amount of NE produced, and thereby have an antihypertensive effect. The DBH inhibitory properties of the compounds of this invention can readily be determined by standard and well-known procedures. For instance, determination of DBH inhibition over time serves to demonstrate the time-dependent kinetics of a DBH inhibitor and is exemplified by a procedure wherein enzymatic oxygenation of a substrate by DBH is determined in aqueous solution in the presence of molecular oxygen, an electron donor such as ascorbate, and the necessary cofactors for the enzyme at a pH of 4.5 to 5.5, preferably pH 5.0, and at a temperature of 20° C. to 40° C., preferably 37° C. The test compound is added at the desired concentration, and the system is incubated. Aliquots are taken at different time intervals and DBH activity is measured using tyramine as the substrate. The reaction is followed by measuring oxygen uptake using a polarographic electrode and an oxygen monitor by the method of S. May, et al., *J. Biol. Chem.*, 256, 2258 (1981). In tests utilizing the above described procedure, the DBH inhibitory activity of the test compounds was found to increase as a function of the time of incubation, as summarized in Table I.

TABLE I

TIME-DEPENDENT DBH INHIBITORY ACTIVITY - IN VITRO

| Compound | Concentration tosylate salt | $t\frac{1}{2}$ +/− Standard error |
|---|---|---|
| 1 | 100 μM | 5.5 min. +/− .54 |
| 2 | 100 μM | 32.7 min +/− 1.4 |
| 3 | 100 μM | 48.1 min +/− 1.5 |
| 4 | 100 μM | 35.6 min. +/− 4.3 |

$t\frac{1}{2}$: time required for 50% log activity remaining
Compound 1: 2-(1,3-dithiolan-2-ylidene)ethanamine
Compound 2: 2-(1,3-dithiol-2-ylidene)ethanamine
Compound 3: 1-(1,3-dithiolan-2-ylidene)-2-propanamine
Compound 4: (E)-2-(dihydro-2(3H)—thienylidene)ethanamine The results in Table I indicate that compound 1 is the most active compound of the compounds tested, as evidenced by the short period of time it requires to inactivate DBH. Although (Z)-2-(dihydro-2(3H)-thienylidene)ethanamine was not active in the time-dependent assay, it is, however, active as an in vivo antihypertensive agent, as described later herein.

The DBH inhibitory properties of the compounds of this invention can also readily be determined in vivo by standard and well known procedures for assaying the conversion of tyramine to octopamine in the presence of DBH, such as the procedure set forth by Feilchenfeld, N. B., Richter, H. W. and Waddell, W. H. in "Time-Resolved Assay of Dopamine Beta Hydroxylase Activity Utilizing High-Pressure Liquid Chromatography", *Analyt. Biochem.*, 122, 124–128 (1982). Determination of the kinetics of DBH inhibition is exemplified by a procedure where the enzyme-assisted conversion of tyramine to octopamine is determined by incubating varying concentrations of test compound with constant concentrations of substrate, enzyme (DBH), molecular oxygen, an electron donor such as ascorbate and the necessary cofactors for the enzyme at optimal temperature and pH. After incubation, the product is separated out by high-performance liquid chromatography and quantitated fluorometrically, from which an inhibition constant ($k_i$) can readily be calculated. 1,3-Dithiolane-2-ethanamine was tested in this manner and a $k_i$ of 11 micro molar was determined, indicating potent activity as a DBH inhibitor.

The ability of the compounds of this invention to lower blood pressure can be determined in vivo by using standard and well-known procedures such as those employed in the continuous recording of arterial blood pressure in conscious animals. For instance, test compounds are administered intraperitoneally (ip) to unanesthetized, spontaneously hypertensive rats and the arterial blood pressure is monitored continuously. In tests utilizing the above described procedure, the antihypertensive effects of the test compounds are readily apparent as indicated by the degree of lowering of mean blood pressure (MBP) noted in Table II.

TABLE II

| ANTIHYPERTENSIVE ACTIVITY-IN VIVO | | | |
|---|---|---|---|
| Compound | Compound Dose mg/kg* | Max Change MBP | % Lowering MBP |
| 1 | 100 ip | −55 +/− 22 | 30.0% |
| 2 | 100 ip | −54 +/− 21 | 28.6% |
| 3 | 200 ip | −39 +/− 21 | 21.7% |
| 4 | 200 ip | −30 +/− 13 | 17.3% |

Compound 1: (E)-2-(dihydro-2(3H)—thienylidene)ethanamine
Compound 2: (Z)-2-(dihydro-2(3H)—thienylidene)ethanamine
Compound 3: 2-(1,3-dithiolan-2-ylidene)ethanamine
Compound 4: 1-(1,3-dithiolan-2-ylidene)-2-propanamine
*Dose was administered as mg/kg tosylate salt.

Thus, based upon these and other standard laboratory techniques known to evaluate DBH inhibitors, by standard toxicity tests and by standard pharmacological assays for the determination of antihypertensive activity in mammals and by comparison of these results with the results of known antihypertensive agents, the effective antihypertensive dosage of the compounds of this invention can readily be determined. In general, effective antihypertensive results can be achieved at a dose of from about 5 to about 100 mg per kilogram body weight per day. Of course, the specific initial and continuing dosage regimen for each patient will vary according to the nature and severity of the hypertension as determined by the attending diagnostician.

In their function as therapeutically useful compounds, it is advantageous to administer the compounds to the host animal in admixture with an acceptable pharmaceutical carrier suitable for administration. Such preparations may be in such forms as, for example, tablets, caplets and suppositories, or in liquid forms such as, for example, elixirs, emulsions, sprays and injectables. The formulation of pharmaceutical preparations can employ substances which do not react with the active ingredient, such as, for example, water, gelatin, lactose, starches, magnesium stearate, talc, vegetable oils, benzyl alcohols, gums, polyalkylene glycols, petroleum jelly and the like. The active ingredient of such pharmaceutical preparations is preferably present in the preparation in such proportions by weight that the proportion by weight of the active ingredient to be administered lies between 0.1% and 50%.

It should be apparent to one of ordinary skill in the art that changes and modifications can be made to this invention without departing from the spirit or scope of the invention as it is set forth herein.

What is claimed is:

1. A compound of the formula

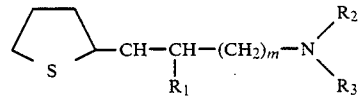

wherein
m is an integer of from 0 to 4, with the proviso that when
m is 0, one of $R_1$, $R_2$, or $R_3$ must be other than hydrogen,
$R_1$ is hydrogen or lower alkyl of from 1 to 6 carbon atoms,
$R_2$ is hydrogen, lower alkyl of from 1 to 6 carbon atoms, hydroxy, amino or amidino, and
$R_3$ is hydrogen or lower alkyl of from 1 to 6 carbon atoms,
and the therapeutically acceptable acid addition salts thereof.

2. A compound of claim 1 wherein $R_1$ is lower alkyl of from 1 to 6 carbon atoms, and $R_2$ and $R_3$ are each hydrogen.

3. A compound of claim 1 wherein $R_2$ is hydrogen or lower alkyl of from 1 to 6 carbon atoms.

4. A compound of claim 1 wherein $R_2$ is amino, hydroxy or amidino, and $R_3$ is hydrogen.

5. A composition comprising a compound according to claim 1 and a pharmaceutically acceptable carrier.

6. A method of treating hypertension in a mammal which comprises administering to said mammal an effective amount of a compound according to claim 1.

* * * * *